(12) United States Patent
Golkowski

(10) Patent No.: US 8,221,679 B2
(45) Date of Patent: Jul. 17, 2012

(54) FREE RADICAL STERILIZATION SYSTEM AND METHOD

(76) Inventor: Czeslaw Golkowski, Ithaca, NY (US)

(*) Notice: Subject to any disclaimer, the term of this patent is extended or adjusted under 35 U.S.C. 154(b) by 535 days.

(21) Appl. No.: 12/510,341

(22) Filed: Jul. 28, 2009

(65) Prior Publication Data

US 2011/0027125 A1    Feb. 3, 2011

(51) Int. Cl.
*A61L 2/00* (2006.01)
*A61L 9/00* (2006.01)
*A62B 7/08* (2006.01)
*B01J 19/08* (2006.01)
*H05F 3/00* (2006.01)
*C01B 13/10* (2006.01)
*F26B 7/00* (2006.01)
*F26B 3/00* (2006.01)

(52) U.S. Cl. ........... 422/1; 422/22; 422/28; 422/30; 422/32; 422/124; 422/125; 422/186.04; 422/298; 422/299; 422/305; 204/164; 204/176; 34/437; 34/443

(58) Field of Classification Search ............ 422/1, 22, 422/28, 30, 32, 124–125, 186.04, 298–299, 422/305; 204/164, 176; 34/437, 443
See application file for complete search history.

(56) References Cited

U.S. PATENT DOCUMENTS

| | | | |
|---|---|---|---|
| 4,863,688 A | 9/1989 | Schmidt et al. | |
| 4,992,247 A | 2/1991 | Foti | |
| 5,173,258 A | 12/1992 | Childers | |
| 5,445,792 A | 8/1995 | Rickloff et al. | |
| 2008/0014113 A1* | 1/2008 | Centanni | 422/27 |

FOREIGN PATENT DOCUMENTS

| | | |
|---|---|---|
| EP | 0298694 | 1/1989 |
| EP | 774263 | 5/1997 |
| EP | 906125 | 4/2004 |
| EP | 1557181 | 7/2005 |
| JP | 4088347 | 3/1992 |
| WO | 8804939 | 7/1988 |
| WO | 9105573 | 5/1991 |
| WO | 9747331 | 12/1997 |

* cited by examiner

*Primary Examiner* — Jill Warden
*Assistant Examiner* — Monzer Chorbaji
(74) *Attorney, Agent, or Firm* — Brown & Michaels, PC

(57) ABSTRACT

A free radical decontamination method and system. The system is comprised of a chamber defining a region, and a generator for generating free radical reach effluent from a free radical electric generator and hydrogen peroxide solution with water. A closed loop circulating system is provided for supplying the mixture of free radicals from the electric generator mixed with the hydrogen peroxide solution in the form of the effluent to the chamber.

29 Claims, 3 Drawing Sheets

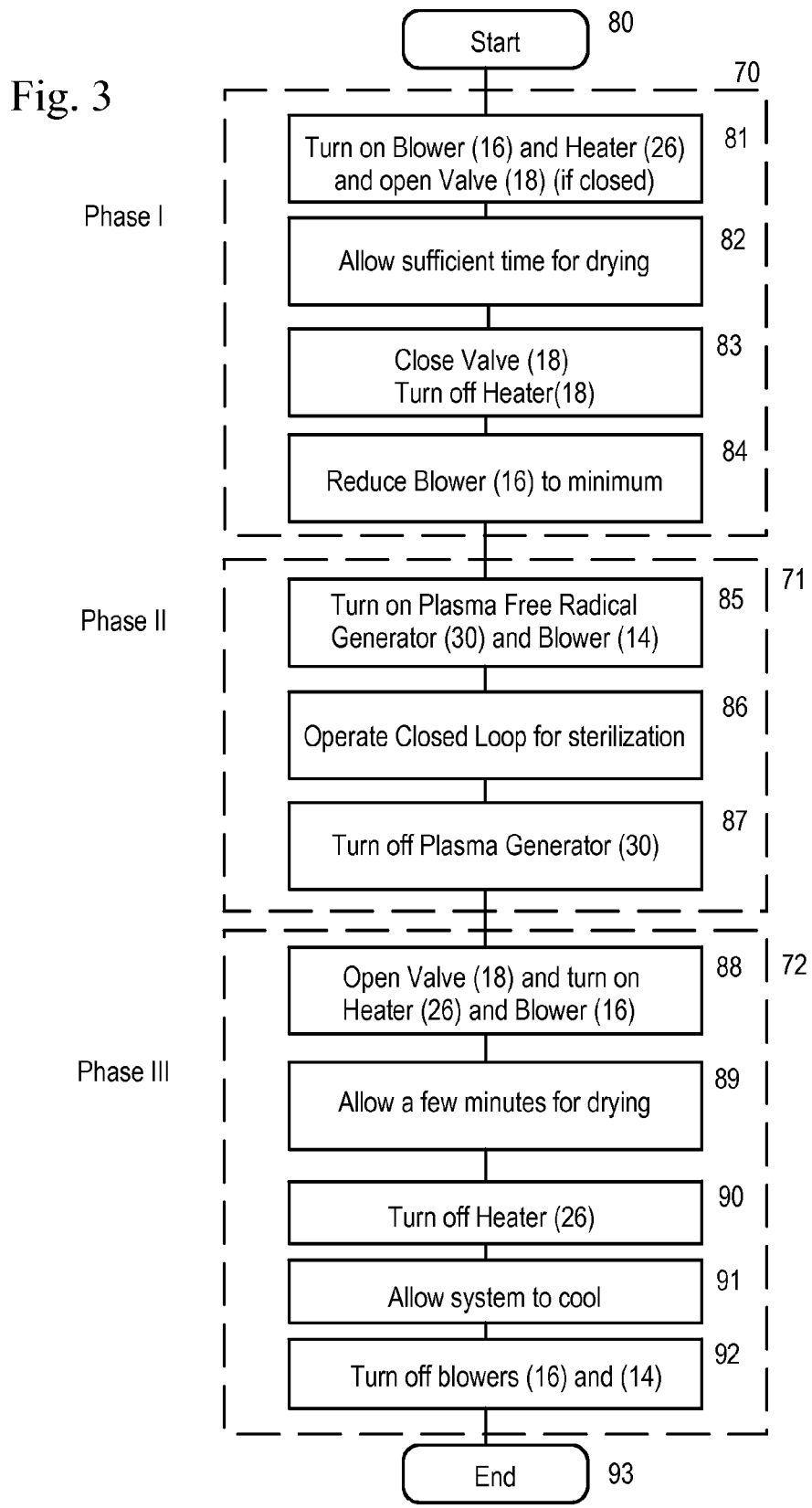

FREE RADICAL STERILIZATION SYSTEM AND METHOD

ACKNOWLEDGMENT OF GOVERNMENT SUPPORT

This invention was made with Government support under Grant No. 0750056, awarded by the National Science Foundation, R44DE017831-03 awarded by NIH. The government has certain rights in the invention.

BACKGROUND OF THE INVENTION

1. Field of the Invention

The present invention relates generally to the art of sterilization and decontamination, and more particularly to a system for sterilization of heat sensitive devices. The present invention also relates to a gaseous sterilization process carried out at atmospheric pressure.

2. Description of Related Art

Sterilization methods are used in a broad range of applications, and have used an equally broad range of sterilization agents. As used herein the term "sterilization" refers to the inactivation of bio-contamination, especially on inanimate objects. The term "disinfection" refers to the inactivation of organisms considered pathogenic.

It is known that pulsed or silent electric discharge in air or other gases produces non-thermal plasma. Non-thermal plasma processing involves producing plasma in which the majority of the electrical energy goes into the excitation of electrons. These plasmas are characterized by electrons with kinetic energies much higher than those of the ions or molecules. The electrons in these plasmas are short-lived under atmospheric pressure; instead they undergo collisions with the preponderant gas molecules. The electron impact on gas molecules causes dissociation and ionization of these molecules, which creates a mix of reactive species, in the form of free radicals, ions and secondary electrons. These reactive species cause unique and diverse chemical reactions to occur, even at relatively low temperatures. These chemical reactions are utilized in low temperature decontamination and sterilization technologies.

It is also known to use vaporized hydrogen peroxide (VHP) for sterilization. Known methods of sterilization with VHP include open loop systems, in which the VHP is applied to the items to be sterilized and then exhausted, and closed loop systems, where sterilizing vapors are recirculated.

In a known closed loop system, a carrier gas, such as air, is dried and heated prior to flowing past a vaporizer. A hydrogen peroxide aqueous solution is introduced into the vaporizer and vaporized. The resulting vapor is then combined with the carrier gas and introduced into a sterilization chamber. A blower exhausts the carrier gas from the sterilization chamber and recirculates the carrier gas to the vaporizer where additional VHP is added. Between the sterilization chamber and the vaporizer, the recirculating carrier gas passes through a catalytic destroyer (where any remaining VHP is eliminated from the carrier gas), a drier, a filter and a heater.

United States Patent Application Publication No: US 2005/0129571 A1 by Centanni discloses a closed loop sterilization system. The purpose of using the closed loop is the increase of the free radical concentration in the circulating effluent. Centanni teaches that there should be a VHP (vapor hydrogen peroxide) destroyer employed in the loop. Cetanni teaches that the ozone is mixed with the hydrogen peroxide vapor and the vapor is produced by injecting hydrogen peroxide water solution on a hot plate and thus evaporating it.

SUMMARY OF THE INVENTION

The present invention provides a method and system for sterilization. Free radicals are generated using a plasma electric discharge generator and passed through a hydrogen peroxide vaporizer to produce highly bactericidal gaseous effluent. The effluent passes through a chamber, and then is recirculated—a portion is routed through the generator, and the generator output is added to the rest of the recirculated effluent to pass back through the vaporizer and again into the chamber, in a closed loop system. The chamber can be in the form of a tumbler to sterilize items like surgical masks or fabrics or medical waste, or in the form of a stationary chamber for more solid items. A blower may be provided inside the chamber to create turbulence.

For use in pre-heating and drying the items to be sterilized, an input conduit equipped with a valve, heater and filter supplies fresh air to the system and an exhaust blower with an upstream filter and a free radical neutralizer removes moisture and active radicals from the system. The exhaust blower may be operated at a low speed mode during sterilization to create a negative-pressure condition in the chamber.

The invention also presents a method of sterilizing items in a chamber using the above-described apparatus. The method includes placing the items in the chamber, pre-heating and drying them in an open-loop, disinfecting using a closed loop circulating system to supply bactericidal free radicals generated by an electric discharge with free radicals in antimicrobial liquid to the chamber, then flushing and drying the system in an open-loop.

BRIEF DESCRIPTION OF THE DRAWING

FIG. 3 shows a flowchart of the method of the invention

DETAILED DESCRIPTION OF THE INVENTION

Figure 1:
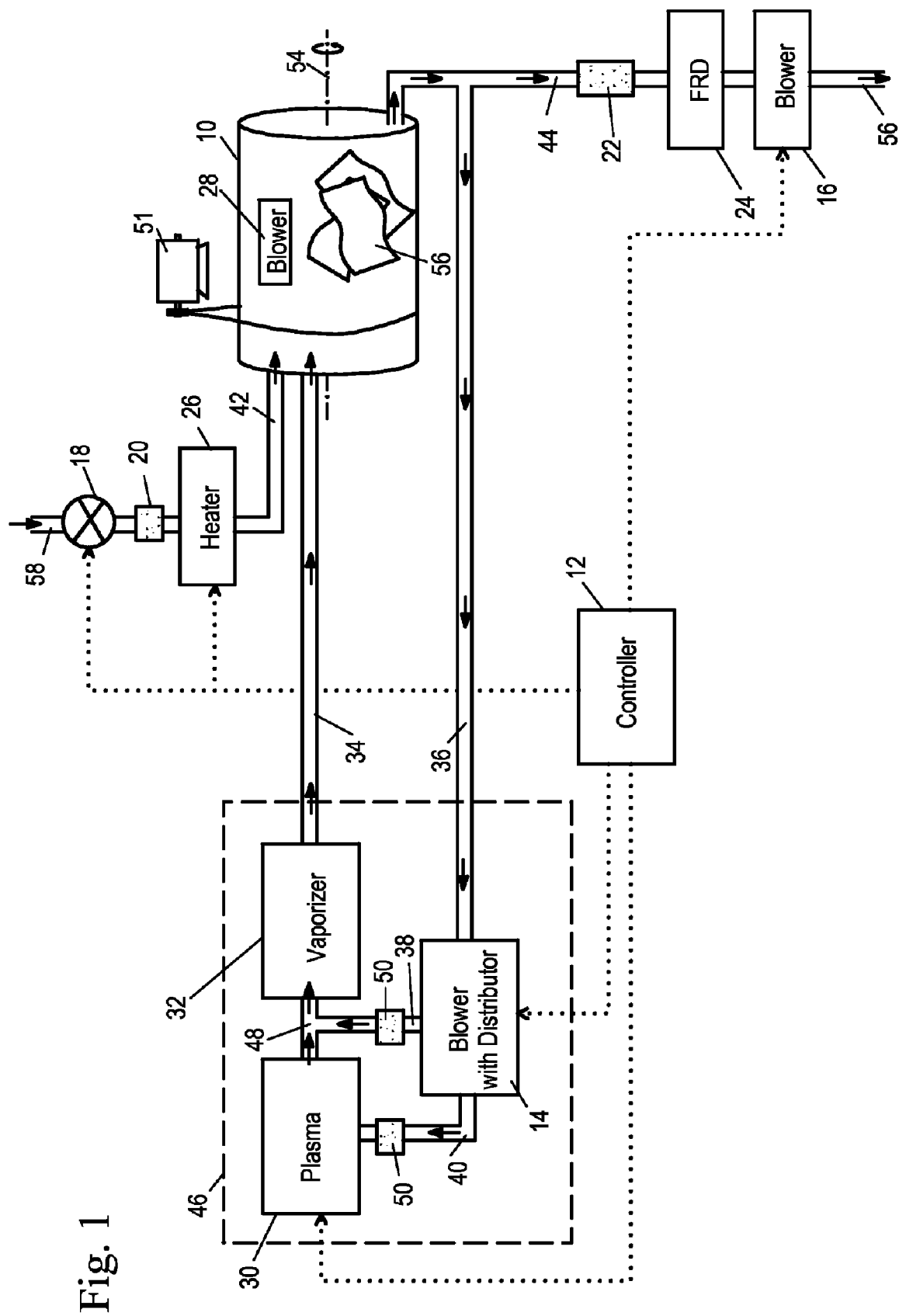
FIG. 1 shows a block diagram of the invention with a tumbler-type chamber
Figure 2:
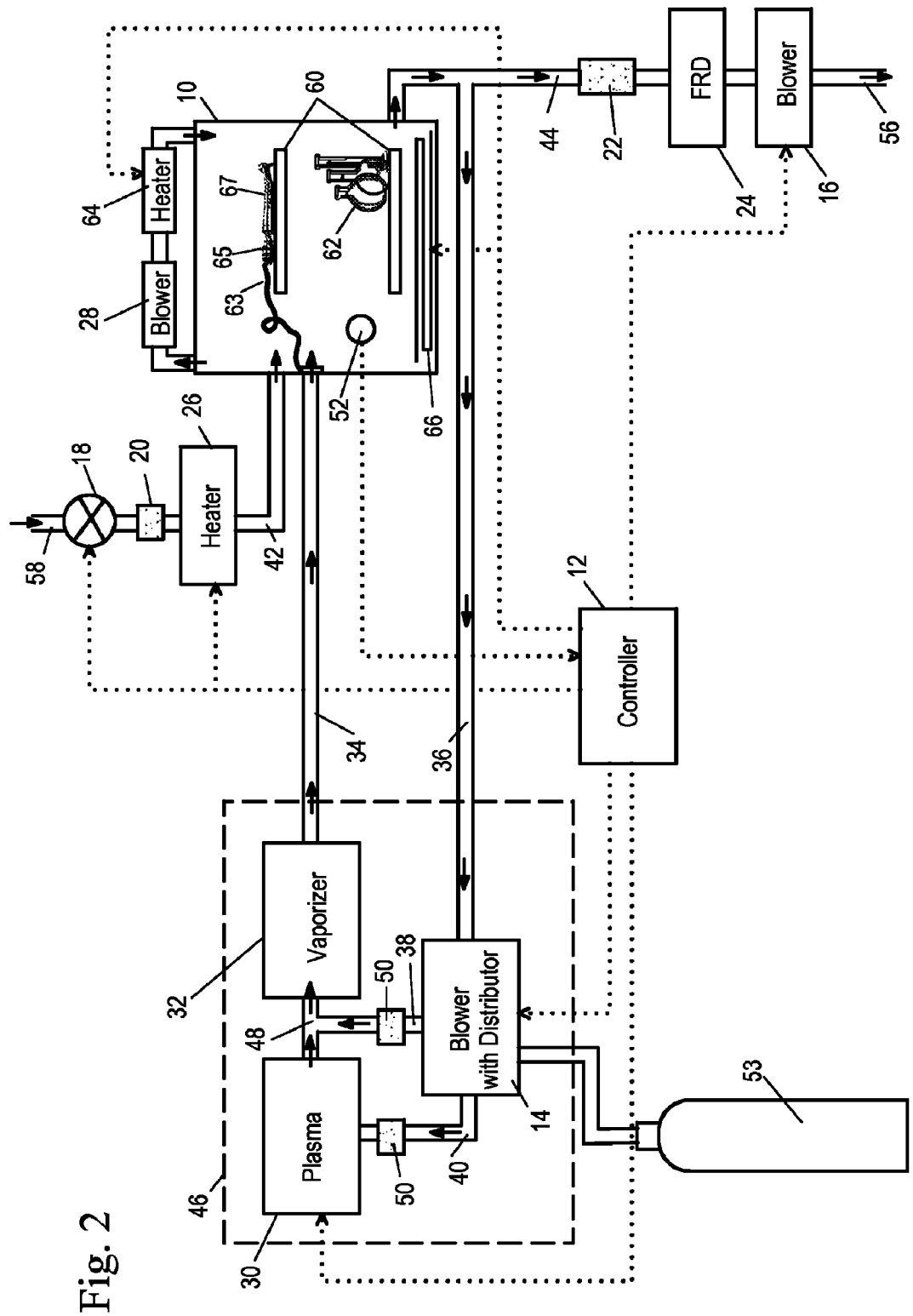
FIG. 2 shows a block diagram of another embodiment of the invention with a stationary chamber with heating

FIGS. 1 and 2 show block diagrams of a sterilization system, illustrating two embodiments of the present invention. Broadly stated, system utilizes a combination of broad mixture of free radicals used in sterilizing and decontamination devices to sterilize items placed in the chamber or chamber.

Details of the Apparatus

Items to be sterilized are placed in a chamber 10. In FIG. 1, the chamber 10 is shown as a tumbler-type chamber, which is rotated around a longitudinal axis 54, for example by motor 51, in the manner of a conventional home clothes dryer. Such a tumbler-type chamber 10 would be appropriate for fabric items 56 such as towels and cloths, surgical masks and gowns, gloves, etc. The tumbler design could also be used to sterilize shredded medical waste within the teachings of the invention.

FIG. 2 illustrates an embodiment appropriate for more rigid items 62, such as laboratory glassware, surgical implements, dental tools, etc. The items 62 may be put on shelves 60, the shelves preferably being made of wire or perforated to allow free circulation of effluent around the items 62.

For the sterilization of instruments with internal conduits or lumens such as endoscopes or dental handpieces 67, a portion of the sterilant gas can be forced through the instruments 67, while the outer surfaces of the instruments 67 are sterilized by the effluent in the chamber, as discussed below. To do this, an additional conduit can be supplied with sterilant gas from the effluent input conduit 34, shown in the figure as flexible hose 63. The hose 63 is equipped with one or more appropriate connectors 65 to plug into the handpiece 67.

Additionally a circulating blower 28 can be used to increase effluent turbulence in the chamber. The blower 28 can be placed in the chamber 10, as shown in FIG. 1, or outside, connected to the chamber by ducts, as shown in FIG. 2. A heater 64 can be put in the ducts to heat the air circulated by the blower 28, or, alternatively, the chamber may be directly heated by elements 66 either in the chamber or attached to the walls of the chamber.

An effluent generator 46 is used for production of effluent for sterilization or decontamination of the chamber and its contents and for powering the circulation of effluent in the closed loop, to be described later. The effluent generator 46 includes a blower with flow distributor 14, a plasma electric free radical generator 30 and a vaporizer 32.

The blower with the flow distributor 14 takes recirculated effluent from the chamber 10 via conduit 36, and distributes it proportionally through conduit 40, which is coupled, optionally through a filter 50, into the plasma generator 30, and through conduit 38, again through optional filter 50, into T-junction 48. The recirculated effluent is preferably distributed in proportions of approximately 30% to conduit 40, and approximate 70% to conduit 38.

Thus, most of the recirculated effluent bypasses the plasma generator 30. The lesser proportion of the effluent passes through generator 30, picking up new free radicals, and is mixed back in the rest of the effluent at T-junction 48. It will be understood that these percentages are for the purpose of example, and other divisions may be chosen within the teachings of the invention.

Optionally, a carrier gas 53, such as air, oxygen, nitrogen, carbon dioxide, helium, argon, or a combination of carrier gases, can be introduced into the effluent generator 46 to be mixed with the effluent in the closed system. This can be done as an additional input to blower/distributor 14, as shown in FIG. 2.

The plasma free radical generator 30 can be any kind of dielectric barrier discharge device. A device which can be used within the teachings of the invention is an ozone generator such as, for example, ozone generator cell SY-G20 manufactured by Longma Industrial Zone, Bao'an District, Shenzhen, 518108, P.R.C.

The mixture of recirculated effluent from blower/distributor 14 and recirculated effluent with additional free radicals from the plasma generator 30 mixes in T-junction 48 and enters vaporizer 32.

The vaporizer 32 contains liquid sterilizing agent such as hydrogen peroxide solution, and the mixture from the T-junction 48, in contact with the solution, produces bactericidal effluent. While the invention is described with particular reference to hydrogen peroxide as the sterilizing agent, it will be appreciated that the system is also applicable to other solutions and pure liquids, such as peracetic acid or formalin solution.

The vaporizer 32 can be in the form of a "bubbler", in which the gas passes through a container of liquid, or the vaporizer could use plates or wicks over which the gas passes, as is known in prior-art devices. Preferably, the vaporizer 32 uses a measured amount of sterilizing agent, preferably in a pre-measured cartridge which can be inserted into the vaporizer, such that the agent is substantially or completely consumed in the course of a sterilizing run. The vaporizer can thus supply a specific small amount of hydrogen peroxide to the evaporator from a cartridge which is empted and dried during the sterilization process. The drying of the cartridge is accomplished by heating it using a small heater and a limited filtered air flow through the cartridge into the system. This way there is no danger that hydrogen peroxide liquid is present in the cartridge at the end of the cycle when a person/operator will insert a new cartridge for next cycle.

The effluent produced in the vaporizer 32 is then introduced into the chamber 10, completing the closed loop of the system.

In addition to the closed loop system, an open loop system is also provided for the purpose of pre-heating and drying the chamber 10 before and after the circulation of bactericidal effluent through the closed loop system. The open loop system uses a blower 16, exhausting to atmosphere 56, to draw air from an air input 58 through input valve 18 and heater 26 into chamber 10. The input air may be filtered by filter 20, which is preferably of the high efficiency particulate air (HEPA) variety. The heated, preferably filtered, air is introduced into the chamber 10 through conduit 42. The input of the blower 16 is connected to the chamber 10 through conduit 44 and a Free Radical Destroyer (FRD) 24, which destroys any free radicals which might remain before the air is exhausted 56. A second filter 22, again preferably of the HEPA type, can be provided in conduit 44 to filter out any particles which would otherwise enter the FRD or be exhausted to the atmosphere. The presence of HEPA filters 20 and 22 at the input and exhaust ensures that there is no microorganism transfer between the ambient air and the sterilization system and vice versa.

The simplest FRD is an activated carbon filter, for example, the Vent Pure "D" from General Carbon Corp. of Paterson, N.J.

By opening valve 18 and turning on heater 26 and blower 16, the chamber 10 and items 56 or 62 within, can be dried and pre-heated before the closed loop operation is begun. Once the pre-heating and drying step is completed, valve 18 is closed and heater 26 is turned off.

Preferably, blower 16 is of a controllable-speed type, so that it may be operated at a reduced speed during closed-loop operation. This will induce a slight negative pressure in the chamber 10, preventing leakage of effluent from the chamber. However, the blower could be a single-speed blower, in which case it would be turned off after the pre-heating step.

After pre-heating, the system is operated in closed-loop mode by starting blower/distributor 14 and plasma generator 30. The effluent mixture circulates continuously through the loop, from generator 46 through conduit 34, through chamber 10 and conduit 36, back to the generator 46.

When this cycle is finished plasma generator 30 is turned off, valve 18 is opened, and blower 16 is turned on full speed in order to remove the active free radicals from the effluent using FRD 24, and to dry the chamber 10 and the sterilized equipment 56 or 62.

The closed loop blower/distributor 14 may remain on, if desired, so as to circulate air through the closed loop to dry the free radical source 46 and vaporizer 32. Heater 26 may optionally be turned on at this stage, as well, so that heated air is circulated through the vaporizer in order to evaporate residual remains of liquid solution of hydrogen peroxide. Alternatively, blower/distributor 14 may be turned off if it is not desired to circulate air through the closed loop portion of the system during this drying step.

A controller 12 is provided in order to control the operation of the various parts of the system. In the embodiment of FIG.

2, a temperature sensor 52 is provided in the chamber 10. The controller 12 can then maintain a selected temperature in the chamber 10 by reading the temperature through sensor 52 and controlling chamber heaters 64 and/or 66 as needed.

Method of Operation

As shown in FIG. 3, the sterilization process consists of three phases:
80—Start the method
70—Phase I—Pre-sterilization drying and heating (Open Loop)
    81—During this phase the exhaust blower 16 is turned on, the valve 18 is opened (if closed) and the heater 26 is turned on. This causes fresh air from the inlet 58 to flow through valve 18, optional HEPA filter 20, and heater 26 into chamber 10 via conduit 42. The heated air dries and heats the sterilized items and is expelled through conduit 42 via optional filter 22, free radical destroyer 24 and exhaust blower 16.
    82—The drying and heating is continued for a sufficient time, for example approximately 5 minutes. If desired, a heat sensor or humidity sensor (not shown) could be provided at the exhaust 56 or in conduit 44, coupled to the controller 12, so that the duration of the pre-heating could be controlled based on empirical data rather than an arbitrary elapsed time. Optionally, if a chamber temperature sensor 52 is provided, the controller 12 may operate heater 26 and, if provided, chamber heaters 64 and/or 66 to maintain a desired pre-heat temperature in the chamber.
    83—After the chamber and the sterilized items are dried and heated the input valve 18 is closed.
    84—The exhaust blower 16 is turned off (or reduced to minimum speed, if this ability is available)
71—Phase II—Sterilization (Closed Loop)
    85—The plasma generator 30 and the closed loop blower/distributor 14 are turned on. This causes the air to circulate in the closed loop through the free radical generator 46 and the chamber 10, as described in the description of the apparatus, above.
    86—The closed loop system produces continuously free radical rich effluent that sterilizes items in the chamber 10. The closed loop operation continues for a time sufficient for sterilization. As an example, a duration of approximately 20-30 minutes should be sufficient for adequate sterilization of most items. If provided, the controller 12 will activate chamber heaters 64 and/or 66 to maintain a desired temperature in chamber 10, as measured by sensor 52.
    87—At the end of the sterilization period, the plasma generator 30 is turned off.
72—Phase III—Post-Sterilization Drying and Clearing (Open Loop)
    88—Input valve 18 is opened, heater 26 is turned on and the exhaust blower 16 is turned on. The closed loop blower/distributor 14 may remain on during this Phase III in order to dry free radical source 46, or, if desired, blower/distributor may be turned off in step 87. The air flows from the input 58 via conduit 42 into the chamber 10 drying the items and, if blower 14 remains on, the free radical source 46. The moist air is expelled into the atmosphere via filter 22 and free radical destroyer 24.
    89—The open loop operation is maintained for a time sufficient to dry and clear the chamber 10. A period of, for example, five minutes should suffice.
    90—Heater 26 is turned off, with blower 16 (and blower 14, if desired) remaining on.
    91—Fresh air is passed through the system for a sufficient time to cool down to the ambient temperature. For example, a few minutes operation would suffice for cooling. Optionally, if sensor 52 is provided in the chamber, the controller 12 could be programmed to continue this cooling until a desired temperature is reached.
    92—Blower 16 is turned off, as well as blower 14 if it is still on. Valve 18 may be closed at this time, or left open for the next run.
93—The method ends. The chamber 10 may now be opened and the items 56/62 removed. New items may be put in the chamber, if desired, and the process repeated again from 80.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention. The drawings are for the purpose of illustrating embodiments of the invention only, and not for the purpose of limiting it.

What is claimed is:

1. A free radical sterilization system comprising:
a) a chamber for containing items to be sterilized;
b) an effluent generator, comprising:
    i) a blower having an inlet coupled to the chamber, a first output and a second output, and a flow distributor for distributing blower flow between the first output and the second output in selected portions;
    ii) a plasma electric free radical generator having an input coupled to the first output of the blower and an output;
    iii) a vaporizer having an input coupled to the second output of the blower and to the output of the plasma electric free radical generator, and an output coupled to the chamber, the vaporizer contacting a liquid sterilizing agent with the output of the blower and free radicals from the free radical generator to produce bactericidal effluent;
such that bactericidal effluent from the effluent generator flows through the chamber and back through the effluent generator in a closed loop;
c) an open loop pre-heater and dryer comprising:
    i) an input valve having an input open to atmosphere and an output;
    ii) a heater having an input coupled to the input valve and an output coupled to the chamber;
    iii) an exhaust blower having an input coupled to the chamber and an output exhausting to atmosphere;
such that air is taken in through the input valve, heated by the heater, passes through the chamber and is exhausted to atmosphere in an open loop.

2. The free radical sterilization system of claim 1, in which the chamber comprises a tumbler.

3. The free radical sterilization system of claim 1, in which the chamber comprises a stationary chamber.

4. The free radical sterilization system of claim 1, in which the liquid sterilizing agent is hydrogen peroxide.

5. The free radical sterilization system of claim 1, in which the vaporizer contains a determined amount of liquid sterilizing agent at a beginning of a sterilization run.

6. The free radical sterilization system of claim 1, in which the flow distributor of the blower distributes 30% of the flow to the first output and 70% to the second output.

7. The free radical sterilization system of claim 1, further comprising a filter between the first output of the blower and the input of the plasma electric free radical generator.

8. The free radical sterilization system of claim 1, further comprising a filter between the second output of the blower and the input of the vaporizer.

9. The free radical sterilization system of claim 1, in which the output of the plasma electric free radical generator and the second output of the blower are coupled together at a junction coupled to the input of the vaporizer.

10. The free radical sterilization system of claim 1, further comprising a filter between the input valve and the heater.

11. The free radical sterilization system of claim 1, further comprising a free radical destroyer between the chamber and the exhaust blower, the free radical destroyer being located in the open loop, and not in the closed loop.

12. The free radical sterilization system of claim 1, further comprising a filter between the chamber and the exhaust blower.

13. The free radical sterilization system of claim 1, further comprising a circulating blower for inducing turbulent flow within the chamber.

14. The free radical sterilization system of claim 13, in which the circulating blower is located within the chamber.

15. The free radical sterilization system of claim 13, in which the circulating blower is located outside the chamber, coupled to the chamber by ducts.

16. The free radical sterilization system of claim 15, further comprising a heater in the ducts coupling the circulating blower to the chamber.

17. The free radical sterilization system of claim 1, further comprising a chamber heater, directly heating the chamber.

18. The free radical sterilization system of claim 17, in which the chamber heater is located within the chamber.

19. The free radical sterilization system of claim 1, further comprising a controller coupled to the blower of the effluent generator, the plasma electric free radical generator, the input valve, the heater, and the exhaust blower.

20. The free radical sterilization system of claim 1, further comprising a source of carrier gas coupled to the closed loop.

21. The free radical sterilization system of claim 20, in which the carrier gas is selected from the group consisting of air, oxygen, nitrogen, carbon dioxide, helium, argon, or a combination of carrier gases.

22. The free radical sterilization system of claim 1, further comprising a conduit for sterilizing interior passages in an instrument, having a first end coupled to the output of the vaporizer and a second end in the chamber having a connector for coupling with the instrument, so that a portion of the effluent passes through the internal passages in the instrument plugged into the connector.

23. A method of sterilization of items in a sterilization chamber using free radicals, comprising:
   a) drying and heating the items in the chamber by drawing heated air through the chamber and exhausting the air from the chamber in an open loop;
   b) circulating free radical rich effluent comprising a mixture of free radicals and a sterilizing agent, in a closed loop from an effluent generator, through the chamber, then back through the effluent generator, the effluent generator comprising a blower for circulating effluent, the blower having an inlet coupled to the chamber, a first output and a second output, a plasma electric free radical generator for generating free radicals having an input coupled to the first output of the blower and an output, and a vaporizer for introducing a sterilizing agent into the effluent having an input coupled to the second output of the blower and to the output of the plasma electric free radical generator;
   c) turning off the effluent generator at the end of a determined sterilization period;
   d) drying and heating the items in the chamber by drawing heated air through the chamber and exhausting the air from the chamber in an open loop; and
   e) cooling the items in the chamber by drawing ambient air through the chamber and exhausting the air from the chamber in an open loop.

24. The method of claim 23, in which air is exhausted during step b, creating a negative pressure in the chamber.

25. The method of claim 23, in which steps d and e further comprise destroying free radicals before exhausting the air using a free radical destroyer.

26. The method of claim 23, in which step a is maintained for a determined period of time.

27. The method of claim 23, in which step a is maintained until a determined temperature or humidity is measured in the exhaust.

28. The method of claim 23, further comprising circulating the air in the chamber with a circulating blower at least during step b.

29. The method of claim 23, further comprising maintaining a determined temperature in the chamber during step b.

* * * * *